(12) United States Patent
Astigarraga et al.

(10) Patent No.: US 11,647,983 B2
(45) Date of Patent: May 16, 2023

(54) AUTOMATING ULTRASOUND EXAMINATION OF A VASCULAR SYSTEM

(71) Applicant: International Business Machines Corporation, Armonk, NY (US)

(72) Inventors: Tara Astigarraga, Fairport, NY (US); Ossama Emam, Giza (EG); Al A. Hamid, Columbus, OH (US); Kimberly Greene Starks, Nashville, TN (US)

(73) Assignee: International Business Machines Corporation, Armonk, NY (US)

( * ) Notice: Subject to any disclaimer, the term of this patent is extended or adjusted under 35 U.S.C. 154(b) by 606 days.

(21) Appl. No.: 15/587,740

(22) Filed: May 5, 2017

(65) Prior Publication Data

US 2018/0317881 A1    Nov. 8, 2018

(51) Int. Cl.
*A61B 8/00* (2006.01)
*A61B 8/08* (2006.01)
*A61B 34/10* (2016.01)
*A61B 34/20* (2016.01)
*A61B 90/00* (2016.01)
(Continued)

(52) U.S. Cl.
CPC .......... *A61B 8/4263* (2013.01); *A61B 8/0891* (2013.01); *A61B 8/461* (2013.01); *A61B 34/10* (2016.02); *A61B 34/20* (2016.02); *A61B 8/488* (2013.01); *A61B 90/13* (2016.02); *A61B 2034/105* (2016.02); *A61B 2034/2065* (2016.02); *A61B 2090/363* (2016.02); *A61B 2090/371* (2016.02); *A61B 2090/372* (2016.02);
(Continued)

(58) Field of Classification Search
CPC . A61B 2090/363; A61B 90/13; A61B 90/378; A61B 34/20; A61B 34/10; A61B 8/42; A61B 2034/2055; A61B 2034/2057; A61B 2034/2065; A61B 2034/2046–2074
See application file for complete search history.

(56) References Cited

U.S. PATENT DOCUMENTS 6,125,197 A    9/2000  Mack et al.
6,146,390 A *  11/2000  Heilbrun .................. A61B 5/06
                                                    606/130
(Continued)

FOREIGN PATENT DOCUMENTS

WO    95/23555 A1    9/1995

OTHER PUBLICATIONS

Peter Mell, "The NIST Definition of Cloud Computing". Special Publication 800-145. Sep. 2011, pp. 1-7.
(Continued)

*Primary Examiner* — Boniface Ngathi N
*Assistant Examiner* — Milton Truong
(74) *Attorney, Agent, or Firm* — Samuel Waldbaum; Otterstedt & Kammer PLLC

(57) ABSTRACT

An ultrasound probe is guided to an optimal position on a patient's body by illuminating the patient's body with a laser, by displaying icons of the probe position and the optimal position on a 3-D model of the patient's body, or by playing an audio signal that varies according to distance of the probe position from the optimal position. In certain embodiments, the probe is guided to a series of optimal positions for conducting a vascular exam, responsive to a database of human anatomy and vasculature and responsive to a database of vascular exam procedures.

25 Claims, 10 Drawing Sheets

(51) Int. Cl.
*A61B 90/50* (2016.01)
*A61B 90/13* (2016.01)

(52) U.S. Cl.
CPC ... *A61B 2090/378* (2016.02); *A61B 2090/502* (2016.02)

(56) References Cited

U.S. PATENT DOCUMENTS

| | | | | |
|---|---|---|---|---|
| 6,149,587 | A * | 11/2000 | Raines | A61B 5/02007 600/300 |
| 2004/0122311 | A1 * | 6/2004 | Cosman | A61B 6/5247 600/427 |
| 2004/0138555 | A1 * | 7/2004 | Krag | A61B 17/32053 600/424 |
| 2006/0079757 | A1 * | 4/2006 | Smith | A61N 5/1049 600/416 |
| 2006/0184021 | A1 | 8/2006 | Kim et al. | |
| 2007/0232886 | A1 * | 10/2007 | Camus | A61B 6/12 600/407 |
| 2009/0088639 | A1 * | 4/2009 | Maschke | A61B 8/4218 600/443 |
| 2010/0249597 | A1 | 9/2010 | Shi | |
| 2010/0286522 | A1 * | 11/2010 | Beach | A61B 5/02007 600/441 |
| 2012/0059249 | A1 * | 3/2012 | Verard | A61B 5/062 600/424 |
| 2013/0053681 | A1 * | 2/2013 | Endo | A61B 6/032 600/443 |
| 2013/0237811 | A1 * | 9/2013 | Mihailescu | A61B 8/5269 600/407 |
| 2014/0107473 | A1 * | 4/2014 | Dumoulin | A61B 17/17 600/424 |
| 2014/0188133 | A1 * | 7/2014 | Misener | A61B 5/06 606/130 |
| 2014/0213905 | A1 | 7/2014 | Saad et al. | |
| 2014/0257104 | A1 * | 9/2014 | Dunbar | A61B 8/14 600/443 |
| 2014/0343431 | A1 | 11/2014 | Vajinepalli et al. | |
| 2014/0350571 | A1 * | 11/2014 | Maillet | A61B 34/20 606/130 |
| 2015/0265852 | A1 * | 9/2015 | Meir | A61B 90/39 348/46 |
| 2016/0022247 | A1 * | 1/2016 | Jin | A61B 8/463 600/440 |
| 2016/0074012 | A1 * | 3/2016 | Forzoni | A61B 8/466 600/440 |
| 2016/0157826 | A1 | 6/2016 | Sisodia et al. | |
| 2016/0235485 | A1 | 8/2016 | Belohlavek et al. | |
| 2017/0136261 | A1 * | 5/2017 | Hofmann | A61N 5/107 |
| 2017/0143303 | A1 * | 5/2017 | Chen | A61B 8/4218 |
| 2017/0252002 | A1 * | 9/2017 | Mine | A61B 8/4218 |
| 2017/0360508 | A1 * | 12/2017 | Germain | G16H 50/50 |

OTHER PUBLICATIONS

John E. Kelly III, "Computing, cognition and the future of knowing", IBM Corp. Oct. 2015, pp. 1-7.

Deepak Sudheendra, "Duplex ultrasound: MedlinePlus Medical Encyclopedia", MedlinePlus, https://medlineplus.gov/ency/article/003433.htm, May 2014, pp. 1-4.

Marie Gerhard-Herman, et al. "Guidelines for Noninvasive Vascular Laboratory Testing: A Report from the American Society of Echocardiography and the Society of Vascular Medicine and Biology", J. Am. Soc Echocardiogr. Aug. 2006, v. 19, p. 955-972.

* cited by examiner

AUTOMATING ULTRASOUND EXAMINATION OF A VASCULAR SYSTEM

BACKGROUND

The present invention relates to the electrical, electronic and computer arts, and more specifically, to medical ultrasound examination equipment.

Medical ultrasound examination equipment has developed rapidly over the past 30 years and is now used routinely for assessment of arterial stenosis, venous incompetence and venous thrombosis. Ultrasound images are obtained by holding a probe on a patient's skin surface. An ultrasonic scanner typically has a range of probes with different characteristics, and for lower limb vascular scanning a linear array probe is normally used. This produces a rectangular image, which is displayed with the skin surface at the top, the vertical axis showing depth into the body and the horizontal axis showing position along the probe.

A duplex ultrasound combines traditional ultrasound with Doppler ultrasound. Traditional ultrasound, sometimes called B-scan, uses sound waves that bounce off blood vessels to create pictures. Doppler ultrasound records sound waves reflecting off moving objects, such as blood, to measure their speed and other aspects of how they flow. Duplex ultrasound combines Doppler flow information and conventional imaging information to allow physicians to see the structure of the blood vessels as well as how blood is flowing through the vessels.

SUMMARY

Vascular ultrasound exams require repetitive, time-consuming steps that impact productivity. Conventional ultrasound exam protocols rely entirely on the training and experience of an ultrasound operator to find and trace the correct blood vessels to be examined. The process depends on human expertise to link and create the full picture and decide on the flow of the examination process (moving the ultrasound scanner along the blood vessel).

Accordingly, principles of the invention provide techniques for automating ultrasound examination of a vascular system.

In one exemplary aspect, a computer-implemented method includes a step of determining an optimal position for placement of an ultrasound scanner on a patient's body, in response to at least a camera image, a database of human anatomy, an exam procedure, and patient information. The method also includes a step of guiding the ultrasound scanner to the optimal position for placement.

In another exemplary aspect, a computer-implemented method includes a step of obtaining, at a processor operatively coupled in communication with a camera, a camera image of a patient's body within a space marked by fiducials. The method also includes a step of calculating, in the processor, based on the camera image, a 3-D model of the patient's body with reference to the fiducials. Further, the method includes a step of establishing, in the processor, based on a vascular exam to be performed and with reference to a 3-D template of human anatomy, a template starting position for placing an ultrasound scanner on the 3-D template. Additionally, the method includes a step of mapping, in the processor, the template starting position from the 3-D template to a modeled starting position on the 3-D model of the patient's body. Further, the method includes a step of determining, in the processor, coordinates of the modeled starting position with reference to the fiducials; and a step of guiding the ultrasound scanner to the coordinates of the modeled starting position.

One or more exemplary aspects of the invention provide a computer-implemented method that includes a step of obtaining a camera image of a patient's body within a space marked by fiducials. The method also includes a step of obtaining an ultrasound image of a vascular structure within the patient's body. The method also includes a step of calculating, based on the camera image, a 3-D model of the patient's body with reference to the fiducials, including coordinates of an ultrasound scanner within the 3-D model. Further, the method includes a step of establishing a path of the vascular structure within the 3-D model, based on the ultrasound image and the coordinates of the ultrasound scanner within the 3-D model. Then the method includes a step of determining coordinates of a next optimal position for the ultrasound scanner, based on the path of the vascular structure and a vascular exam procedure to be performed; and a step of guiding the ultrasound scanner to the coordinates of the next optimal position.

One or more exemplary embodiments of the invention provide an apparatus, which includes a memory storing computer executable instructions; a camera; an ultrasound scanner; and at least one processor, coupled to the memory. The at least one processor is configured according to the computer executable instructions to facilitate a method. The method includes a step of obtaining from the camera a camera image of a patient's body within a space marked by fiducials, as well as a step of calculating, based on the camera image, a 3-D model of the patient's body with reference to the fiducials. The method further includes a step of establishing, based on a vascular exam to be performed and with reference to a 3-D template of human anatomy, a template starting position for placing an ultrasound scanner on the 3-D template. The method also includes a step of mapping the template starting position from the 3-D template to a modeled starting position on the 3-D model of the patient's body, and a step of determining coordinates of the modeled starting position within the 3-D model with reference to the fiducials. Additionally, the method includes a step of guiding the ultrasound scanner to the coordinates of the modeled starting position.

One or more exemplary embodiments of the invention provide an apparatus, which includes a memory storing computer executable instructions; a camera; an ultrasound scanner; and at least one processor, coupled to the memory, and configured according to the computer executable instructions to facilitate a method. The method includes a step of obtaining from the camera a camera image of a patient's body within a space marked by fiducials, and includes a step of obtaining from the ultrasound scanner an ultrasound image of a vascular structure within the patient's body. The method also includes a step of calculating, based on the camera image, a 3-D model of the patient's body with reference to the fiducials, including coordinates of the ultrasound scanner within the 3-D model. The method also includes a step of establishing a path of the vascular structure within the 3-D model, based on the ultrasound image and the coordinates of the ultrasound scanner within the 3-D model. Additionally, the method includes a step of determining coordinates within the 3-D model of a next optimal position for the ultrasound scanner, based on the path and the vascular exam procedure to be performed. Finally, the method includes a step of guiding the ultrasound scanner to the coordinates of the next optimal position.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments provide one or more of:

Automated guidance for initial placement of an ultrasound probe on a patient's anatomy.

Real-time alerting of vascular abnormality.

Automated guidance for probe traversal along a patient's vasculature.

These and other features and advantages of the present invention will become apparent from the following detailed description of illustrative embodiments thereof, which is to be read in connection with the accompanying drawings.

DETAILED DESCRIPTION

Figure 1:
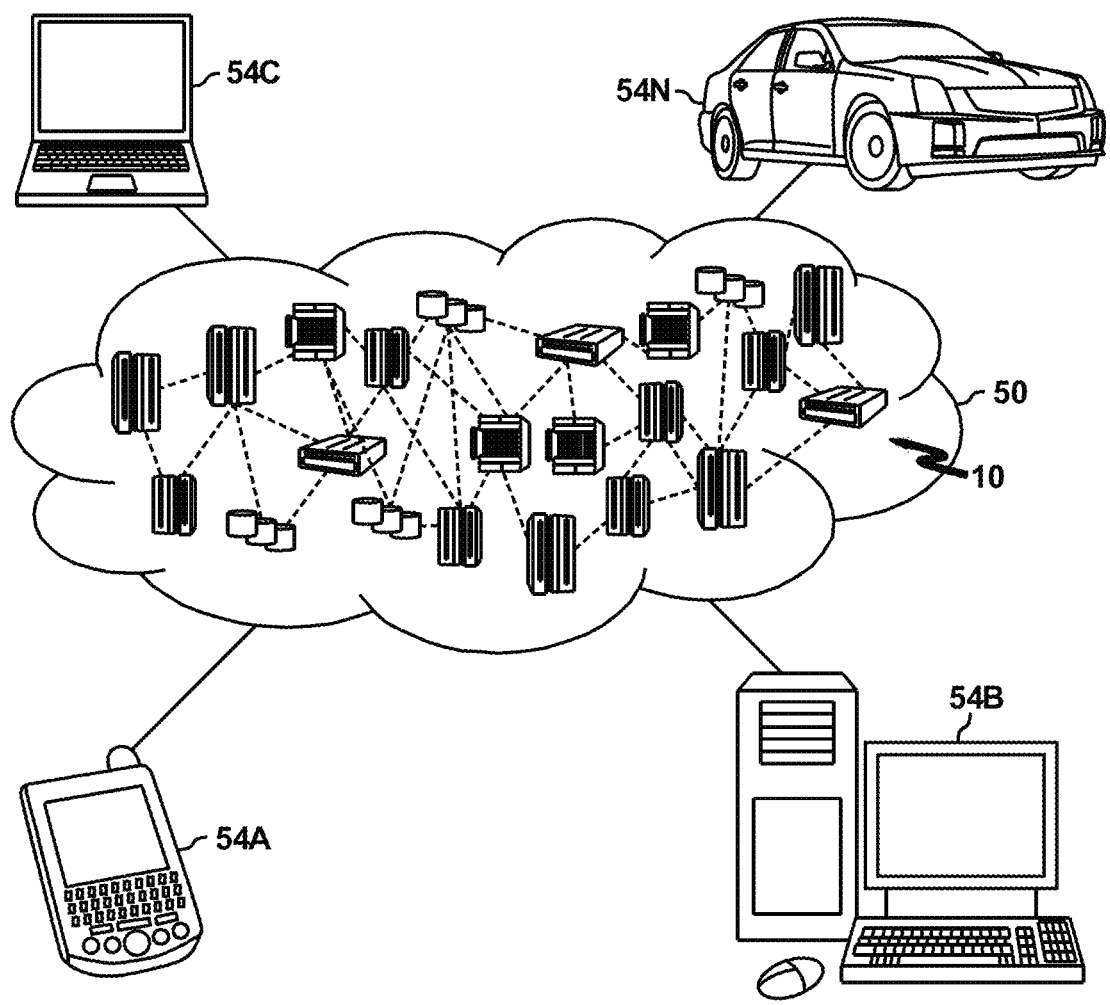
FIG. 1 depicts a cloud computing environment according to an embodiment of the present invention.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
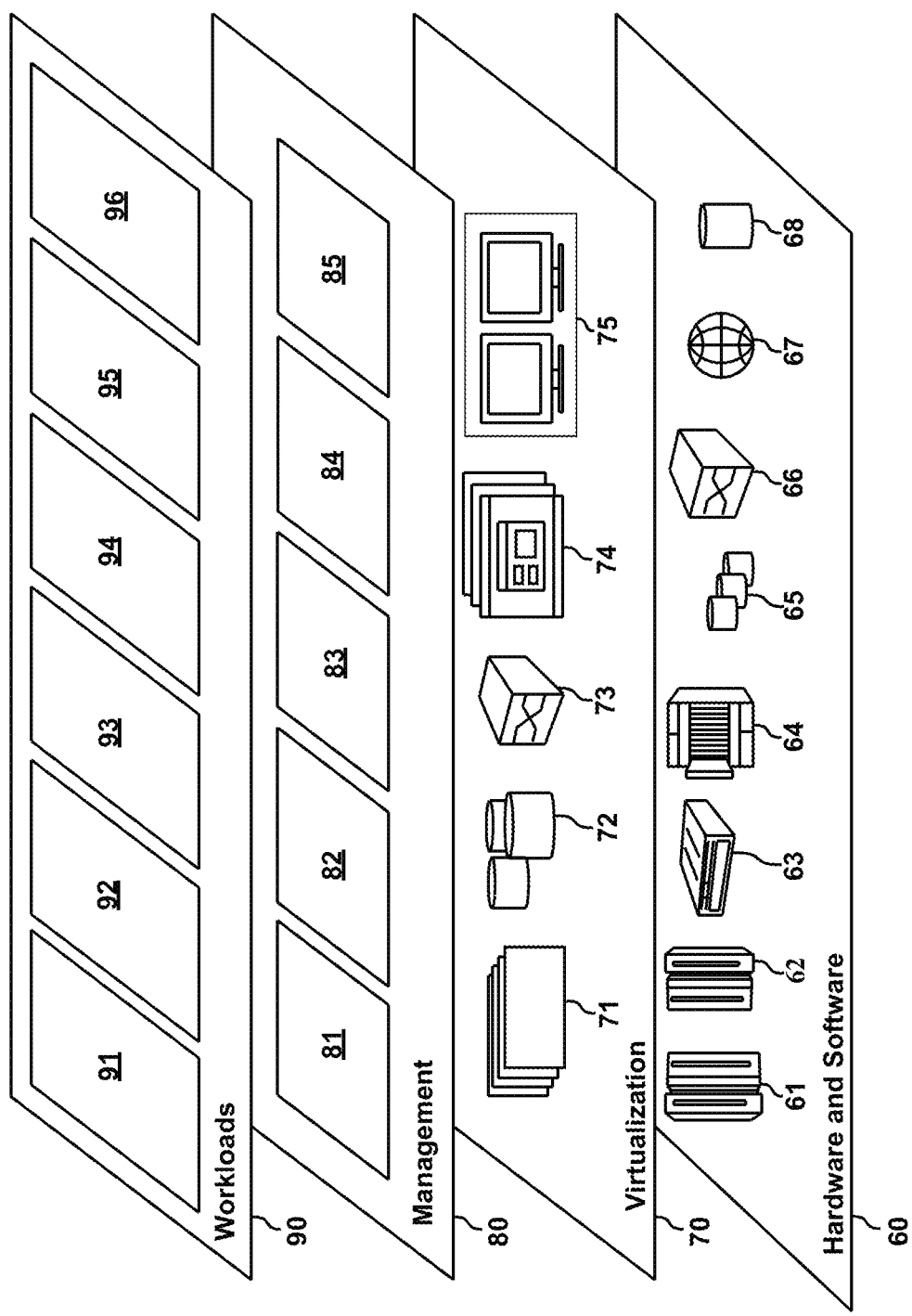
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and an intelligent vascular exam assistant system ("I-VEAS") 96.

Figure 3:
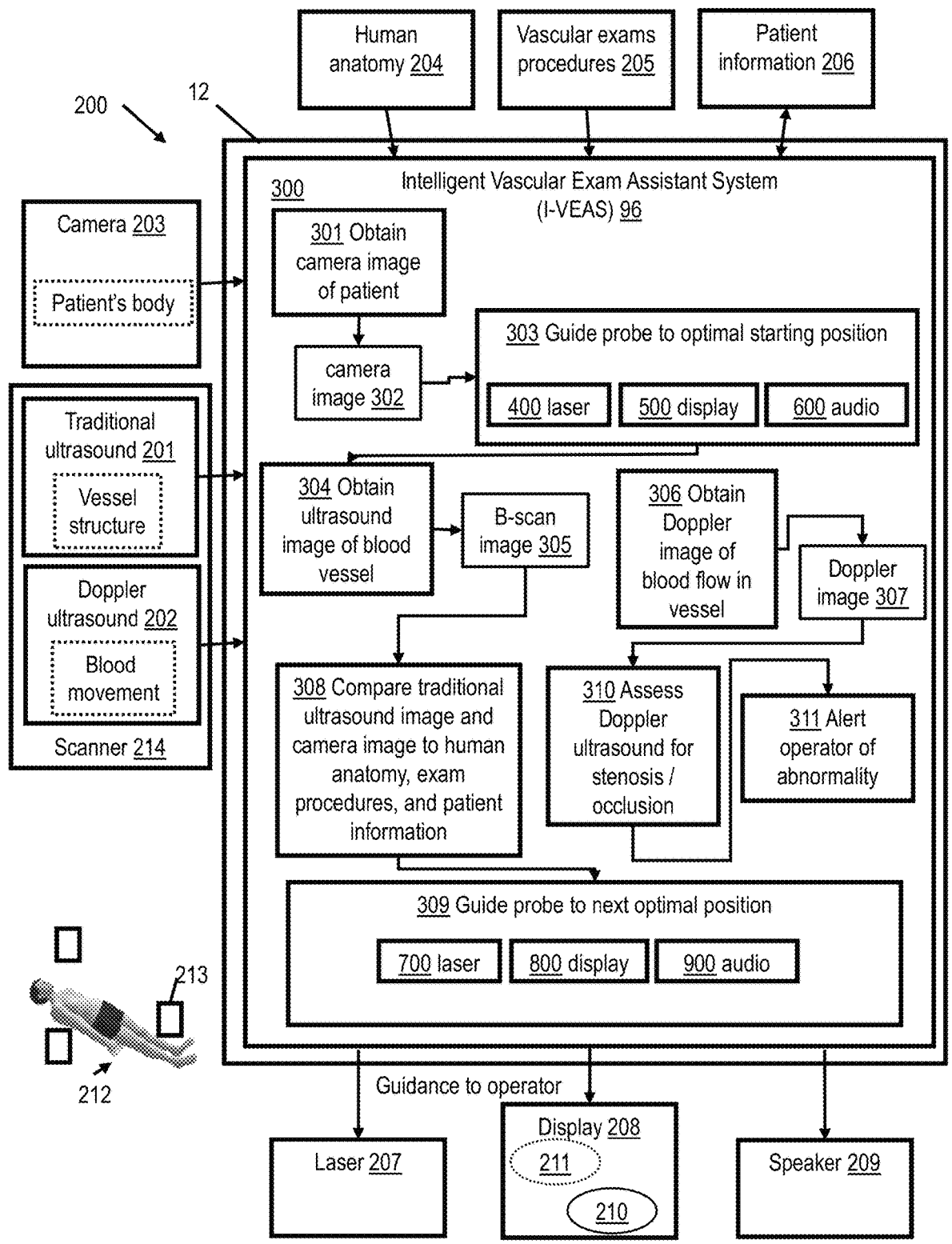
FIG. 3 depicts an ultrasound exam apparatus including an intelligent vascular exam assistant system, and a method of examination that is implemented by the apparatus, according to one or more exemplary embodiments of the invention.
Figure 10:
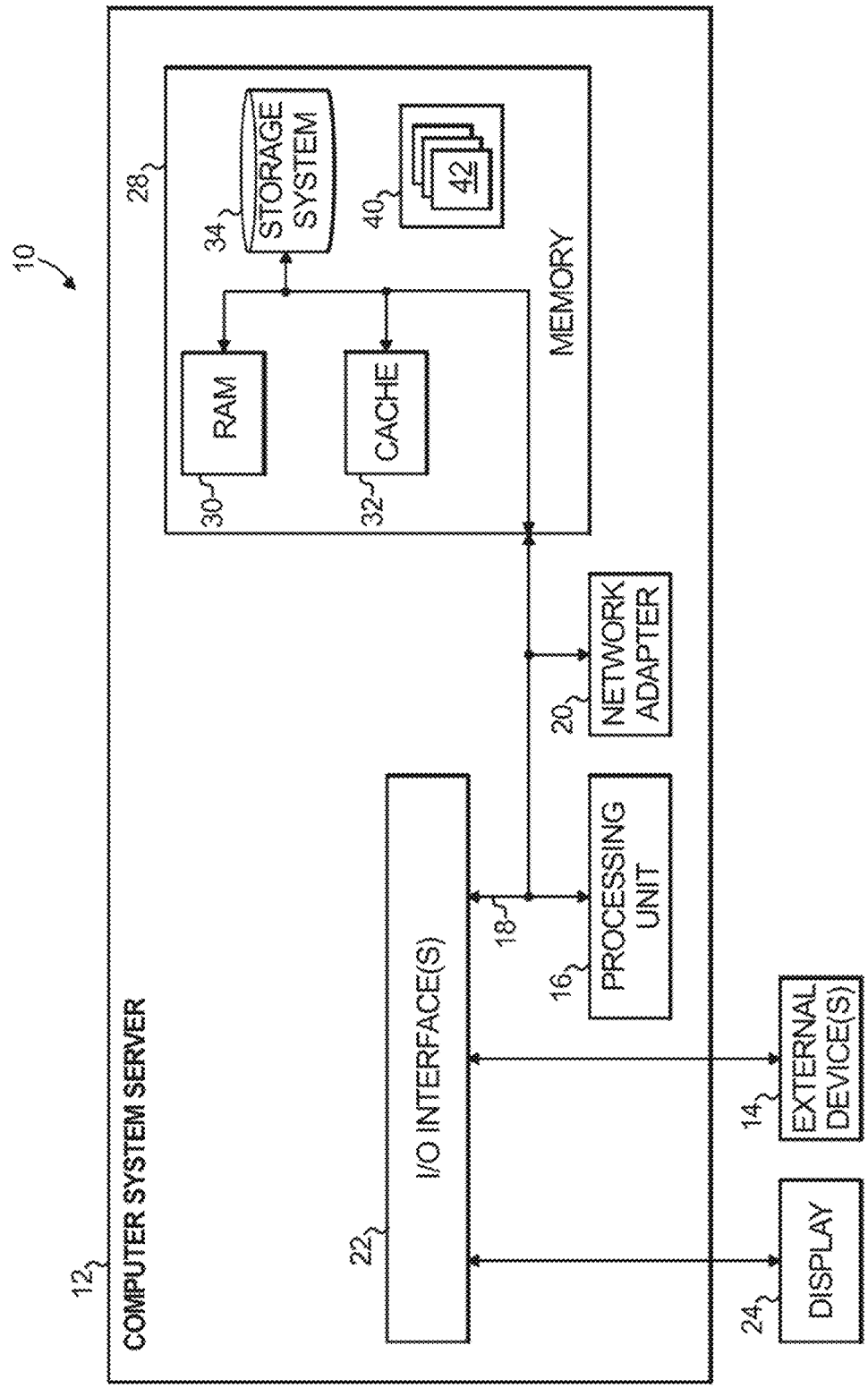
FIG. 10 depicts a computer system that may be useful in implementing one or more aspects and/or elements of the invention, also representative of a cloud computing node according to one or more exemplary embodiment of the present invention.

FIG. 3 depicts an ultrasound exam apparatus 200 that incorporates the I-VEAS 96, and a method of examination 300 that is implemented by the system 200, according to one or more exemplary embodiments of the invention. Within the apparatus 200, the I-VEAS 96 is operatively coupled in communication with ancillary devices and databases. According to one or more embodiments, the I-VEAS 96 is implemented in a computing system 12 (further described below with reference to FIG. 10). With reference to FIG. 10 the computing system 12 is described as being incorporated in a node 10 of the cloud computing system 50, however, in one or more exemplary embodiments the computing system 12 is a stand-alone component of the apparatus 200.

The ancillary devices to the I-VEAS 96 include a traditional ultrasound probe 201, which provides data related to vascular structure; a Doppler ultrasound probe 202, which provides data related to blood flow; and a camera 203, which provides a camera image 302 of the patient's body.

The traditional ("B-scan") ultrasound probe 201 transmits and receives sound waves that bounce off blood vessels, and is operatively coupled in communication with a computer that measures the sound wave echo times to create two-dimensional images that allow an operator (and the I-VEAS 96) to see the structure of the blood vessels. The Doppler ultrasound probe 202 transmits and records sound waves reflecting off moving objects (such as blood cells), and is operatively coupled in communication with a computer that measures the sound wave echo times and frequency shifts to determine the speed of the blood cells and other aspects of how they flow. Together, the traditional and Doppler ultrasound probes provide data that show the operator (and the I-VEAS 96) how blood is flowing through the vessels. In one or more embodiments, the two ultrasound probes 201, 202 are housed in a common housing. The common housing will hereafter be referred to as an ultrasound scanner 214. The ultrasound scanner 214 can be handheld by an operator or can be moved by a robotic arm in response to computer instructions, for example in response to the movements of a remote operator in telemedicine or the like. According to one or more embodiments, the ultrasound scanner 214 may be moved by computer instructions that are generated in response to the I-VEAS 96 generating a series of optimal positions for placing the ultrasound scanner.

As will be further discussed hereafter, the I-VEAS 96 uses the camera image 302 in guiding an operator of the apparatus 200 to correctly position the ultrasound scanner.

The ancillary devices also include a laser 207, which can be utilized to illuminate the patient; a display 208, which can be utilized to provide text or image information to an operator of the I-VEAS 96; and a speaker 209, which can be utilized to provide an audio signal to the operator. According to one or more embodiments, the display 208 may be incorporated into an augmented reality (AR) or virtual reality (VR) headset. A VR headset display 208 may be particularly helpful in telemedicine embodiments of the invention. The databases include human anatomy 204, vascular exams procedures 205, and patient information 206. In one or more embodiments, the human anatomy database 204 is structured as a 3-D template of a statistically averaged body with "normal" vasculature.

The I-VEAS 96 is a cognitive computing system. That is, the I-VEAS 96 is a computer or network of computers configured to understand (read unstructured data, such as ultrasound images, and extract information), to reason (build hypothesis about which way to move an ultrasound scanner), and to learn (uses machine learning techniques to learn from data, such as whether an operator's movement of the ultrasound scanner tracks a target blood vessel). Generally, the I-VEAS 96 includes one or more computer processors that are configured to work together to implement one or more machine learning algorithms. The implementation may be synchronous or asynchronous. In the I-VEAS 96, the processor(s) simulate thousands or millions of neurons, which are connected by axons and synapses. Each connection is enforcing, inhibitory, or neutral in its effect on the activation state of connected neural units. Each individual neural unit has a summation function which combines the values of all its inputs together. In some implementations, there is a threshold function or limiting function on at least some connections and/or on at least some neural units, such that the signal must surpass the limit before propagating to other neurons. The I-VEAS 96 can implement supervised, unsupervised, or semi-supervised machine learning. In supervised or semi-supervised machine learning the I-VEAS 96 is provided with a set of sample input data and sample output data, and adjusts the connections between the simulated neurons until it can produce the sample output data from the sample input data. Then the I-VEAS 96 is provided with a new set of input data to produce a new set of output data. In unsupervised machine learning, the I-VEAS 96 is provided only with input data, and outputs a categorization of the input data in response to patterns that it identifies in the input data. Thus, the I-VEAS 96 extracts useful information from the vascular exams procedure 205 (which blood vessel needs to be traced for each different vascular exam) and the patient information 206 (which vascular exam needs to be performed), and will complement with the human anatomy knowledge 204 (where the blood vessels are likely to be located in the patient's body).

For the convenience of the reader, the inventive system and method will be discussed with reference to a clinical example. The chosen clinical example is an arterial vascular exam of the lower limb.

The anatomy 204 of the lower limb: Blood is normally supplied to the leg through a single main artery, which has different names in different parts of the leg: common and external iliac arteries in the lower abdomen, common and superficial femoral arteries in the thigh, and popliteal artery behind the knee. Below the knee the lower limb artery branches into the smaller posterior tibial, peroneal and anterior tibial arteries.

The vascular exams procedures 205 of the lower limb: Patient supine on the bed. Use a curvilinear 3-5 MHz (megahertz) transducer. Put coupling gel on the thigh from groin to knee over the path of the artery. Place the scanner on the skin in the groin and identify the common femoral artery identified using the B-scan display. Switch the scanner to duplex mode, and obtain the blood velocity waveform in the common femoral artery using color Doppler scan. The peak systolic blood velocity normally lies between 90 and 140 cm/s. Values significantly above this may indicate local stenosis, while values below can indicate low flow caused by proximal or distal occlusion. Note the presence of any plaque intruding into the lumen, and estimate the degree of any stenosis. Then move the scanner along the artery until the origin of the profunda femoris artery is identified using the B-scan display. This is usually just beyond the skin crease in the groin. Obtain the blood velocity waveform at the origin, note the waveform shape and record the presence of any stenosis. Mark the position of the origin on the skin surface using a water-soluble crayon. Examine the superficial femoral artery along its length using the color Doppler display. A significant stenosis is normally taken to be one that more than doubles the blood velocity. Mark the site of any significant stenosis on the skin surface and record the distance from the vessel origin and the increase in velocity.

The patient information 206: Age=44, Height=178 cm. The reason for scanning the lower limb arteries is to locate and assess any narrowing (stenosis) or blockage (occlusion).

Thus, in conducting the exemplary lower limb vascular exam, the I-VEAS 96 will establish based on the patient information 206 that the desired exam is of the lower limb artery. From the human anatomy knowledge 204, the I-VEAS 96 will establish that the lower limb artery (femoral artery) follows a path through the patient's thigh, starting at the groin and ending at the knee. Additionally, from the vascular exams procedures 205 the I-VEAS 96 will establish that a first step is to place the ultrasound scanner at the patient's groin, and that subsequent steps include identifying the common femoral artery (by analyzing the structural data obtained via the traditional ultrasound), instructing an operator to switch the ultrasound scanner to duplex mode, and using Doppler ultrasound to measure the blood velocity waveform in the common femoral artery and then in the superficial femoral artery.

Accordingly, the I-VEAS 96 is configured to implement the method 300 for performing the lower limb vascular exam. The two main purposes of the method 300 are to find the correct vessel and to follow the correct vessel. Therefore, the I-VEAS 96 is configured to guide placement of the ultrasound scanner in an initial area to find the correct vessel, and to guide subsequent movement of the ultrasound scanner to follow the correct vessel.

According to an exemplary embodiment of the present invention, the method 300, performed by the I-VEAS 96, includes obtaining 301, from the camera 203, a camera image 302 of the patient on whom the exam is to be performed. Note that the camera "image" may include multiple images, e.g., a stereoscopic image. In response to the camera image 302 and based on its knowledge of the human anatomy database 204, the I-VEAS will perform a step 303 of guiding the operator's initial placement of the ultrasound scanner at an optimal starting position on the patient's body. Guidance can be accomplished by various modes. For example, guidance of the scanner can be by a method 400 of illuminating the patient's body, using the laser 207, at the optimal position of the scanner 214 (see FIG. 4); by a method 500 of displaying an image of the supine patient (which may be the camera image, or a 3-D model of the patient), using the display 208, with an icon 210 indicating the actual position of the scanner and another icon 211 indicating the optimal position of the scanner 214 (see FIG. 5); or by a method 600 of playing an audio signal, using the speaker 209, that varies (e.g., in frequency, volume, melody, or beat) based on the distance of the scanner 214 from its optimal position (see FIG. 6). These various modes of guidance will be described below with reference to FIGS. 4-6. According to various embodiments of the invention, two or more modes of guidance may be used in combination. Other modes of guiding the scanner will be apparent to the skilled worker.

Figure 4:
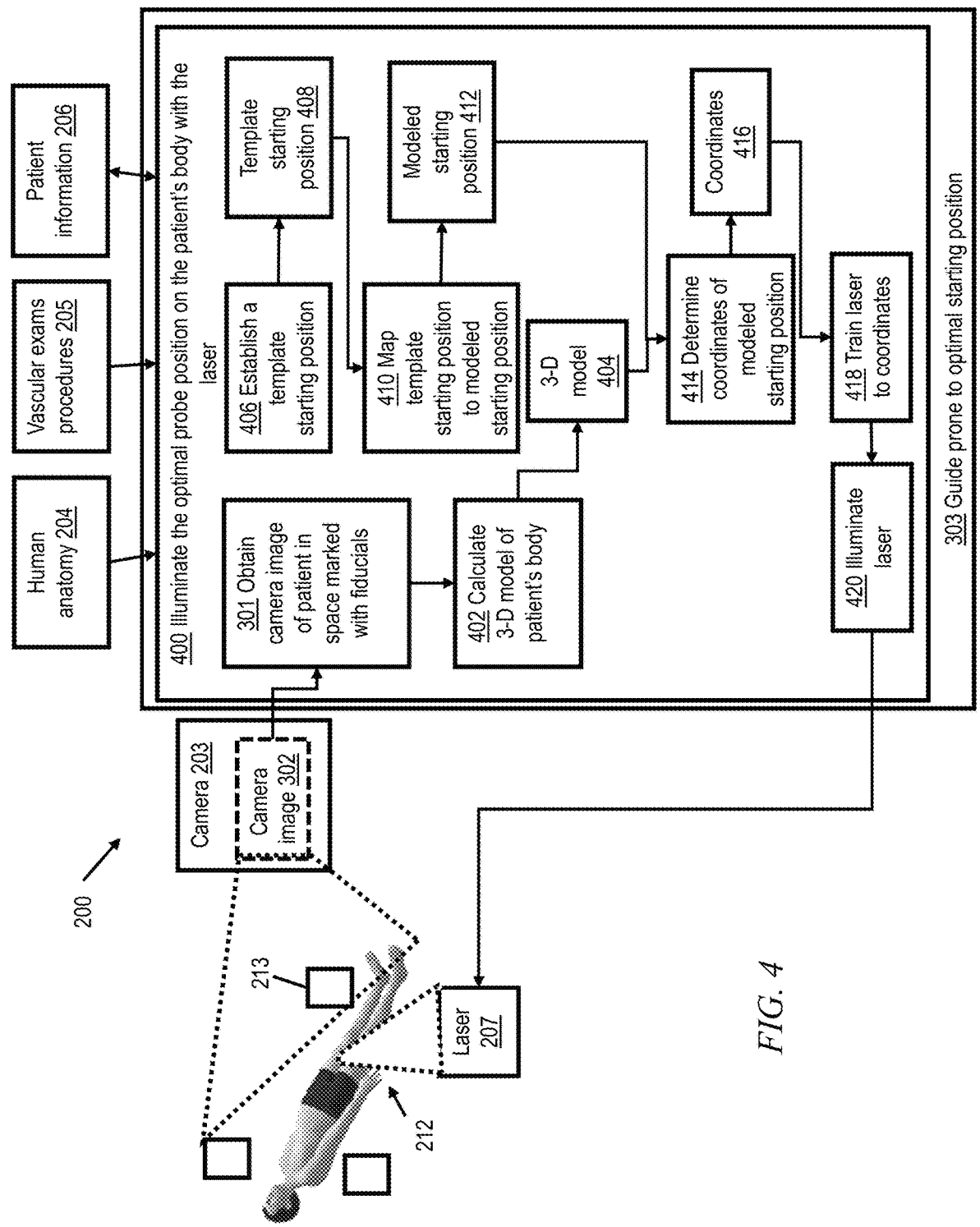
FIG. 4 depicts a method for guiding an ultrasound scanner to an optimal starting position on the patient's body, using a laser, according to embodiments of the invention.

FIG. 4 depicts steps of the method 400 according to an exemplary embodiment of the present invention by which the I-VEAS 96 causes the laser 207 to illuminate the optimal starting position on the patient's body. Notably, when illuminating the patient's body with the laser 207, a position and angle for shining the laser 207 can be determined responsive to the camera image 302 of the patient's body, the human anatomy database 204, and the vascular exams procedures 205.

The method 400 includes the step 301 of obtaining the camera image 302 of a patient's body 212 within a space marked by fiducials 213 and a step 402 of calculating, based on the camera image 302, a 3-D model 404 of the patient's body 212 with reference to the fiducials 213. The method 400 also includes a step 406 of establishing, based on a vascular exam 205 to be performed and with reference to the 3-D template of human anatomy 204, a template starting position 408 for placing an ultrasound scanner on the 3-D template. Because the patient's body 212 will not exactly match the 3-D template 204, which may for example be based on statistically averaged anatomy, the method 400 also includes a step 410 of mapping the template starting position 408 from the 3-D template 204 to a modeled starting position 412 on the 3-D model 404 of the patient's body. The method 400 then includes a step 414 of determining coordinates 416 of the modeled starting position with reference to the fiducials 213, using the 3-D model 404. The method 400 also includes using motors (not shown for clarity) to accomplish a step 418 of training the laser 207 within the fiducial-marked space to the coordinates 416 of the modeled starting position 412. Then the I-VEAS 96 completes the step 420 of illuminating the patient's body with the laser 207 to indicate the optimal starting position for the scanner.

Figure 5:
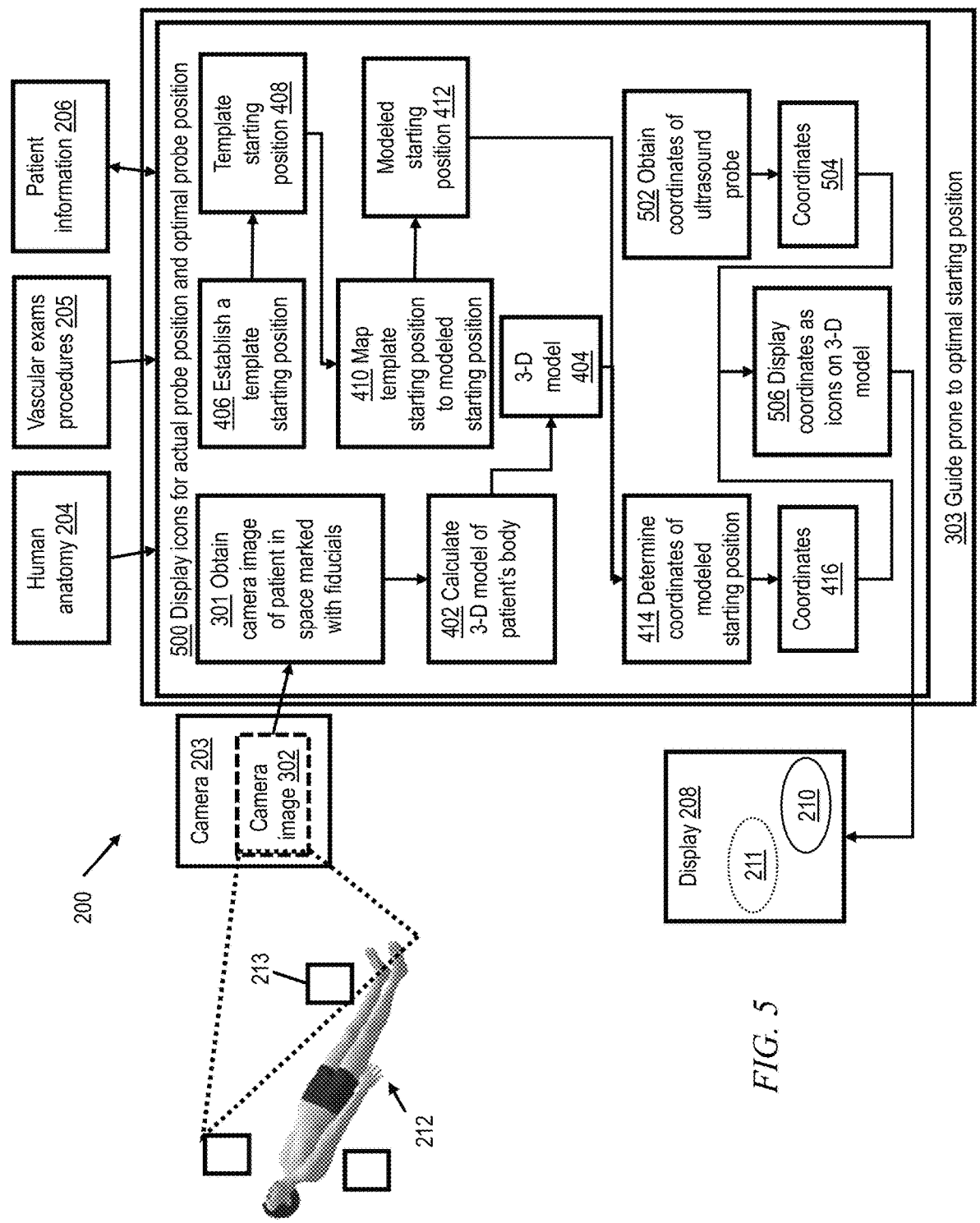
FIG. 5 depicts a method for guiding an ultrasound scanner to an optimal starting position on the patient's body, using a visual display, according to one or more exemplary embodiments of the invention.

FIG. 5 depicts steps of the method 500 according to an exemplary embodiment of the present invention by which the I-VEAS 96 causes the display 208 to show a 3-D image of the supine patient, with an icon 210 indicating the actual position of the scanner and another icon 211 indicating the optimal position of the scanner.

The method 500 includes the step 301 of obtaining the camera image and the step 402 of calculating the 3-D model 404. The method 500 also includes the step 406 of establishing the template starting position 408. The method 500 also includes the step 410 of mapping the template starting position 408 from the 3-D template 204 to a modeled starting position 412 on the 3-D model 404. The method 500 then includes the step 414 of determining coordinates 416 of the modeled starting position 412. At this point the method 500 diverges from the method 400, in that the method 500 also includes a step 502 of obtaining coordinates 504 of the ultrasound scanner within the space marked by the fiducials 213. For example, in some embodiments the step 502 is accomplished by interaction of the scanner with the fiducials, e.g., wireless triangulation of the 3-D scanner coordinates with reference to the fiducials. In one or more embodiments, the step 502 is accomplished by computer image analysis of the scanner's position within the camera image 302. The method 500 then includes a step 506 of displaying the ultrasound scanner coordinates 504 and the modeled starting position coordinates 416 at the visual display 208, as icons 210, 211 superimposed on the 3-D model 404 or on the camera image 302.

Figure 6:
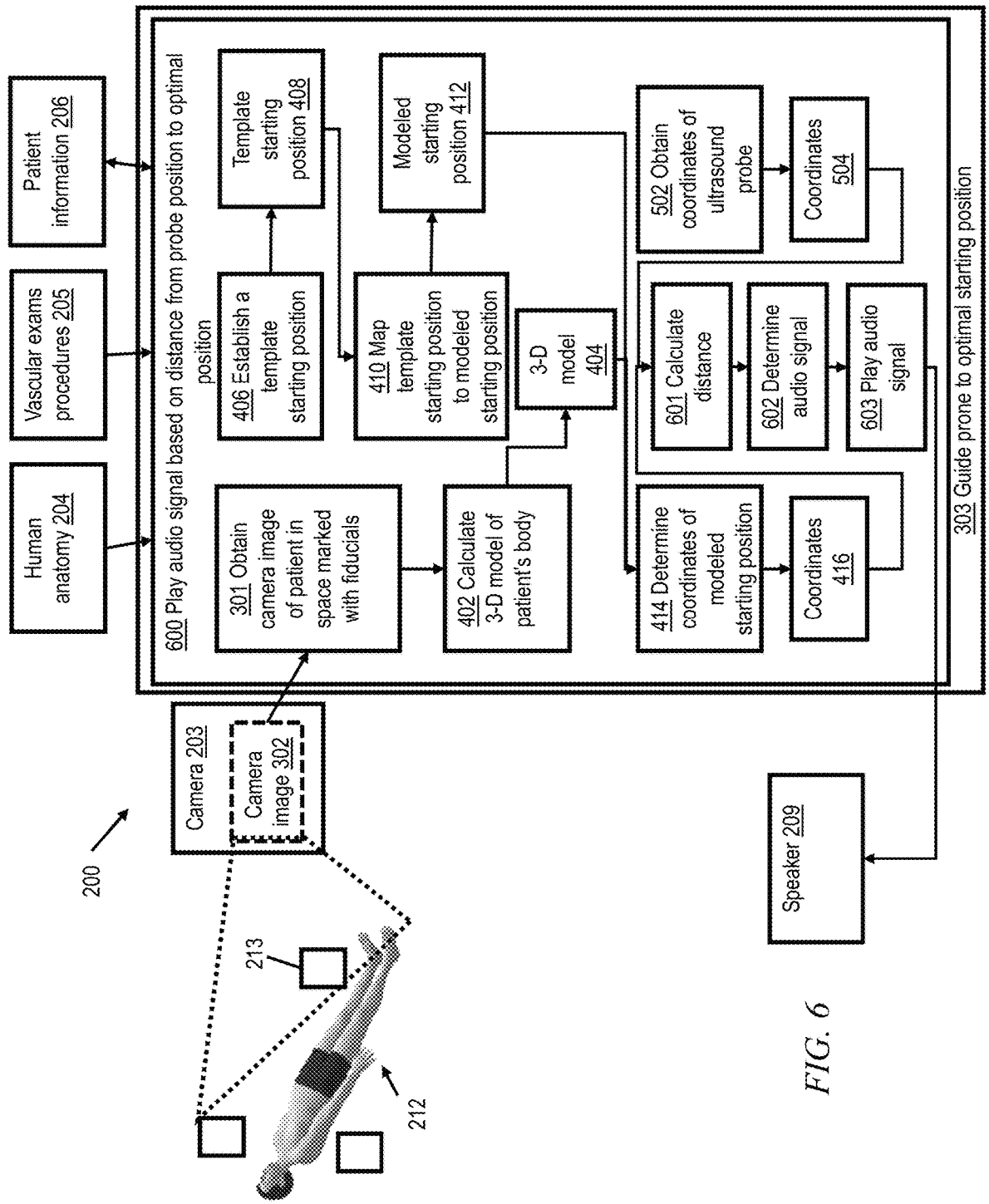
FIG. 6 depicts a method for guiding an ultrasound scanner to an optimal starting position on the patient's body, using an audio signal, according to one or more exemplary embodiments of the invention.

FIG. 6 depicts steps of the method 600 according to an exemplary embodiment of the present invention by which the I-VEAS 96 causes the speaker 209 to play an audio signal that varies according to a distance of the scanner from an optimal position.

The method 600 includes the step 301 of obtaining the camera image and the step 402 of calculating the 3-D model 404. The method 600 also includes the step 406 of establishing the template starting position 408. The method 600 also includes the step 410 of mapping the template starting position 408 from the 3-D template 204 to a modeled starting position 412 on the 3-D model 404. The method 600 then includes the step 414 of determining coordinates 416 of the modeled starting position 412. The method 600 also includes the step 502 of obtaining coordinates 504 of the ultrasound scanner. At this point the method 600 diverges from the methods 400 and 500, in that the method 600 includes a step 601 of calculating a distance from the coordinates of the ultrasound scanner to the coordinates of the modeled starting position. The method 600 also includes a step 602 of determining, based on the calculated distance, at least one of a frequency, volume, melody, or beat for an audio signal; and a step 603 of playing the audio signal through the speaker 600.

Referring again to FIG. 3, during initial placement of the ultrasound scanner, and thereafter throughout the procedure, the I-VEAS 96 will continue to obtain 301 the camera image 302 of the patient's body and will continue to obtain coordinates 504 of the ultrasound scanner. Additionally, the I-VEAS 96 will obtain 304 a traditional ("B-scan") ultrasound image 305 of blood vessel position with reference to the ultrasound scanner as well as obtain 306 a Doppler ultrasound image 307 of blood flow in the blood vessel. The I-VEAS 96 will compare 308 the traditional ultrasound image 305 and the camera image 302 to its knowledge of human anatomy 204, exam procedures 205, and patient information 206 in order to determine where to move the ultrasound scanner to follow the correct blood vessel. The I-VEAS 96 then will perform a step 309 of guiding the scanner movement to a next optimal position, according to any of the several modes discussed above with reference to FIGS. 4-6. For example, the I-VEAS 96 may illuminate 700 the patient with the laser 207 to show a next scanner position; or display 800 icons of the scanner coordinates 504 and of an optimal position for the scanner, superimposed on the 3-D model 404 of the patient's body; or play 900 an audio signal, through the speaker 209, that varies (e.g., in frequency, volume, melody, or beat) according to whether the scanner is moving in the right direction. According to various embodiments of the invention, two or more modes of guidance may be used in combination. Other modes of guiding the scanner will be apparent to the skilled worker. Thus, throughout guidance of the scanner the I-VEAS 96 confirms to the operator whether the scanner has been moved to a proper position. For example, when the scanner is optimally positioned the I-VEAS 96 plays a pleasant tone through the speaker 209, displays a pastel hue at the display 208, or slowly pulses the laser 207. On the other hand, in this example, while the scanner is not optimally positioned the I-VEAS 96 plays an off-key tone through the speaker 209, displays a garish hue at the display 208, or rapidly blinks the laser 207.

Figure 7:
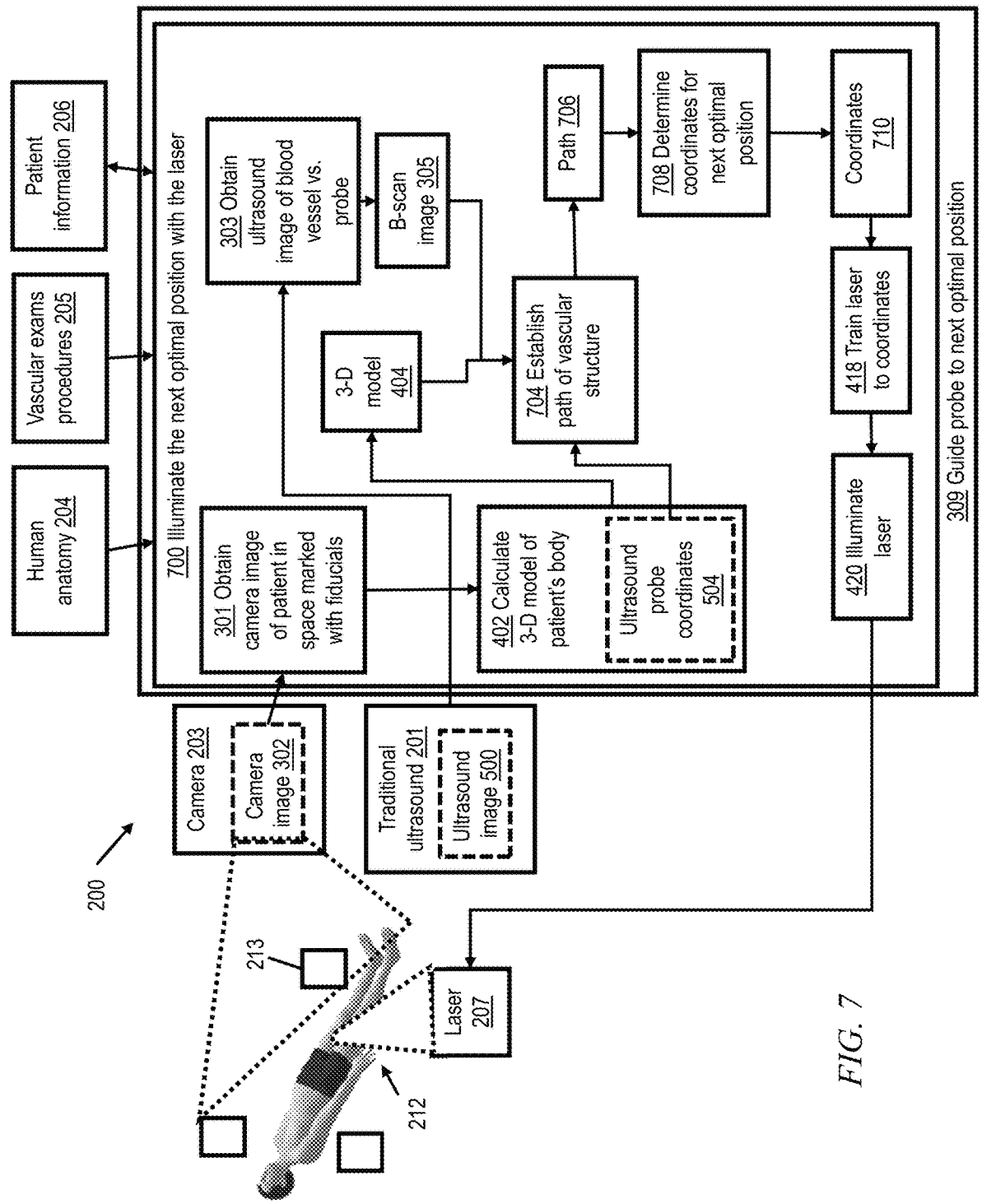
FIG. 7 depicts a method for guiding an ultrasound scanner to a next optimal position along a vascular structure, using a laser, according to one or more exemplary embodiments of the invention.

For example, with reference to FIG. 7, a method 700 for guiding the ultrasound scanner to a next optimal position along a vascular structure, using the laser 207, includes the step 301 of obtaining the camera image 302 of the patient's body 212 within the space marked by fiducials 213, then a step 402 of calculating the 3-D model 404 of the patient's body. Further, the 3-D model 404 may include the ultrasound scanner coordinates 504 that are obtained as discussed above with reference to FIGS. 5 and 6. According to at least one embodiment of the present invention, based on the ultrasound image 305 and the ultrasound scanner coordinates 504, the method 700 includes a step 704 of establishing a path 706 of the vascular structure within the 3-D model 404. Then the method 700 includes a step 708 of determining coordinates 710 of a next optimal position for the ultrasound scanner 202 based on the vascular exam procedure 205 and the vascular structure path 605. The method 700 proceeds to the step 418 of directing the laser 207 to the coordinates 710 within the space marked by the fiducials 213, then to the step 420 of illuminating the patient's body with the laser.

Figure 8:
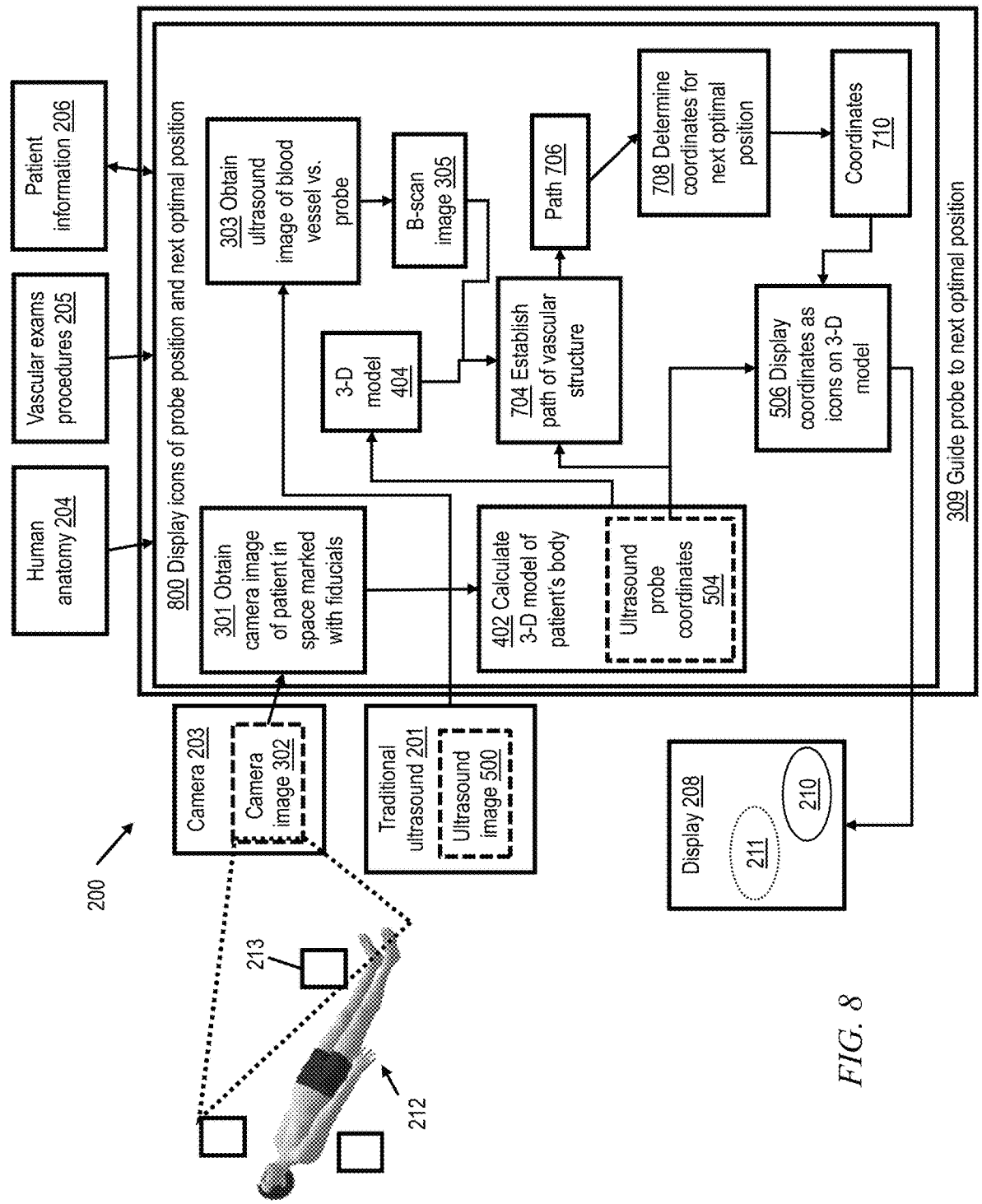
FIG. 8 depicts a method for guiding an ultrasound scanner to a next optimal position along a vascular structure, using a visual display, according to one or more exemplary embodiments of the invention.

FIG. 8 illustrates another method 800 according to an exemplary embodiment of the present invention for guiding the ultrasound scanner to a next optimal position along a vascular structure, using the visual display 208. The method 800 includes the step 301 of obtaining the camera image 302, the step 402 of calculating the 3-D model 404, the step 704 of establishing a path 706 of the vascular structure, and the step 708 of determining coordinates 710 of the next optimal position for the ultrasound scanner 202. Then the method 800 proceeds to the step 506 of displaying the ultrasound scanner coordinates 504 and the next optimal position coordinates 710 as icons 210, 211 at the visual display 208.

Figure 9:
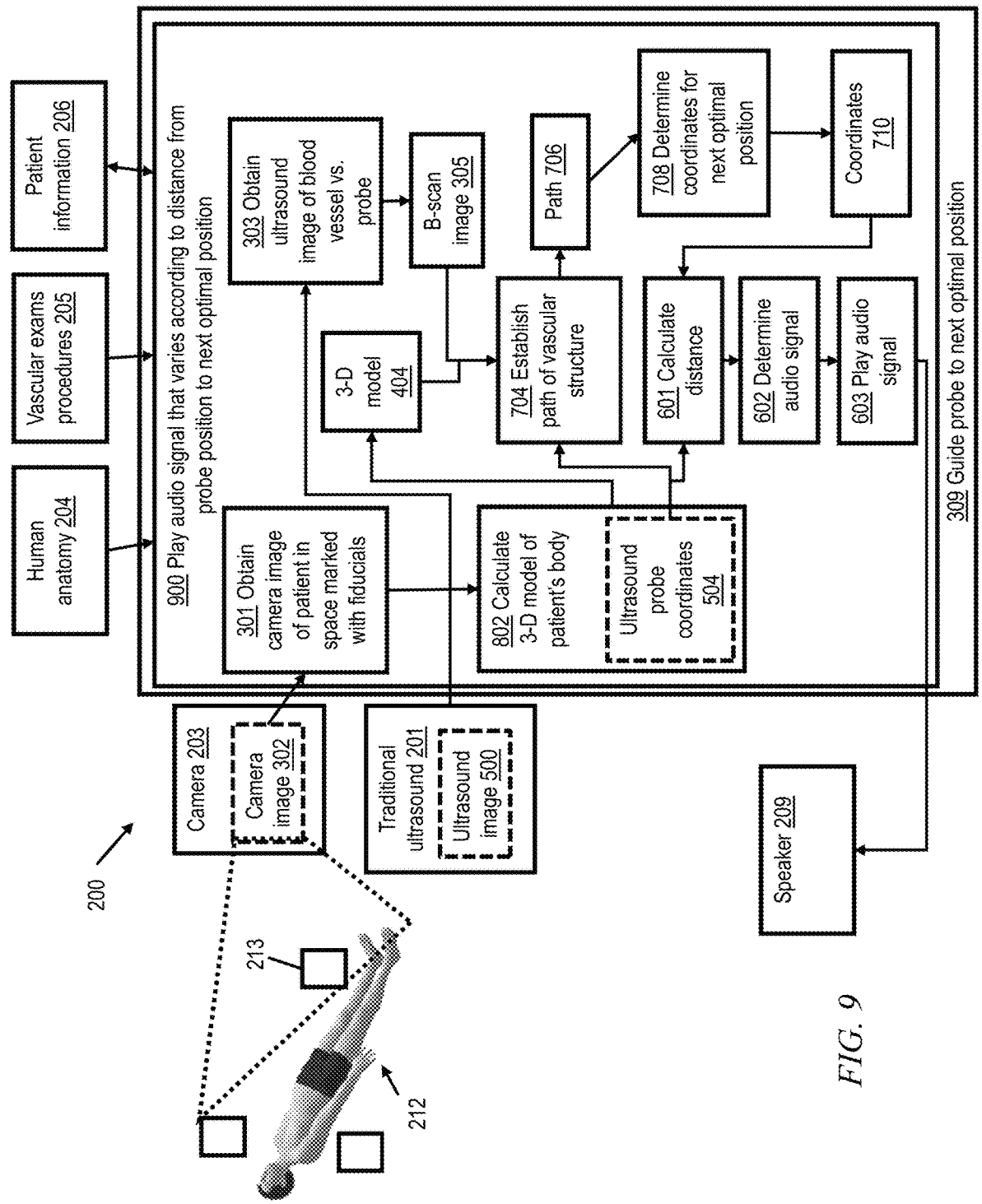
FIG. 9 depicts a method for guiding an ultrasound scanner to a next optimal position along a vascular structure, using an audio signal, according to one or more exemplary embodiments of the invention.

FIG. 9 depicts another method 900 according to an exemplary embodiment of the present invention for guiding the ultrasound scanner to a next optimal position along a vascular structure, using the speaker 209. The method 900 includes the step 301 of obtaining the camera image 302, the step 402 of calculating the 3-D model 404, the step 704 of establishing a path 706 of the vascular structure, and the step 708 of determining coordinates 710 of the next optimal position for the ultrasound scanner 202. Then the method 900 proceeds to the step 601 of calculating a distance between the ultrasound scanner coordinates 504 and the next optimal position coordinates 710, the step 602 of determining an audio signal to generate in response to the calculated distance, and the step 603 of playing the audio signal through the speaker 209.

Referring again to FIG. 3, while guiding movement of the ultrasound scanner, the I-VEAS 96 also will facilitate a step 310 of assessing the B-scan or Doppler ultrasound data for a vascular abnormality, for example, stenosis or occlusion of an artery. As mentioned above, peak systolic blood velocity normally lies between 90 and 140 cm/s. Values significantly above this may indicate local stenosis, while values below can indicate low flow caused by proximal or distal occlusion. In case the I-VEAS 96 detects any such abnormality, it will estimate the degree of stenosis or occlusion and incorporate that estimate into the patient information 206. The I-VEAS 96 also will facilitate a step 311 of alerting the operator. The alert may be by text or image at the display 208, by an audio signal via the speaker 209, and/or by illuminating the patient with the laser 207 to mark the approximate location of the abnormality (for example, the I-VEAS 96 may cause the laser to blink in a pattern or color distinct from patterns or colors that indicate on-track or off-track scanner position). Such laser illumination will be helpful to the operator in making a less ephemeral marking with a water-soluble crayon or the like.

Given the discussion thus far, and with reference to the drawing Figures, it will be appreciated that, in general terms, an exemplary computer-implemented method 300, according to an aspect of the invention, includes a step 406 of determining an optimal position for placement of an ultrasound scanner on a patient's body, in response to at least a camera image 302, a database of human anatomy 204, an exam procedure 205, and patient information 206. The method 300 also includes a step 303 or 309 of guiding the ultrasound scanner to the optimal position for placement. According to one or more implementations of the exemplary method 300, the step 303 or 309 of guiding the scanner includes at least one of illuminating the patient's body 212 with a laser 207 at the optimal position, displaying at a display 208 a 3-D model or an image of the patient's body with an icon 211 marking the optimal position, and playing through a speaker 209 an audio signal that varies according to a distance of the scanner from the optimal position. Guiding the ultrasound scanner also may include displaying at the display 208 an icon 210 marking the position of the scanner.

In at least one exemplary embodiment, the method 300 includes a step 310 of assessing ultrasound data from the scanner for a vascular abnormality. Further, the method 300 includes estimating a degree of stenosis or occlusion; and incorporating the estimate into the patient information. Additionally, the method 300 includes a step 311 of alerting an operator to the presence of the vascular abnormality. For example, alerting can include at least one of illuminating the patient's body with a laser at an approximate location of the vascular abnormality, displaying text or an image at a display, and playing an audio signal through a speaker.

According to another exemplary aspect of the invention, a computer-implemented method 300 includes a step 301 of obtaining, at a processor 16 operatively coupled in communication with a camera 203, a camera image 302 of a patient's body 212 within a space marked by fiducials 213. The method 300 also includes a step 402 of calculating, in the processor, based on the camera image 302, a 3-D model 404 of the patient's body with reference to the fiducials 213. Further, the method 300 includes a step 406 of establishing, in the processor 16, based on a vascular exam to be performed and with reference to a 3-D template of human anatomy 204, a template starting position 408 for placing an ultrasound scanner on the 3-D template. Additionally, the method 300 includes a step 410 of mapping, in the processor, the template starting position 408 from the 3-D template 204 to a modeled starting position 412 on the 3-D model of the patient's body. Further, the method 300 includes a step 414 of determining, in the processor, coordinates 416 of the modeled starting position with reference to the fiducials 213; and a step 303 of guiding the ultrasound scanner to the coordinates of the modeled starting position. For example, in one or more implementations of the invention, guiding the ultrasound scanner includes a step 418 of the processor operating motors to direct a laser 207 to the coordinates of the modeled starting position, and a step 420 of illuminating the patient's body with the laser. In one or more implementations of the invention, guiding the ultrasound scanner includes a step 502 of obtaining coordinates 504 of the ultrasound scanner with reference to the fiducials 213, and a step 506 of displaying an icon 210 for the ultrasound scanner coordinates and an icon 211 for the modeled starting position, superimposed on the 3-D model 404, at a visual display 208 that is operatively coupled in communication with the processor 16. For example, in some implementations, the coordinates 504 of the ultrasound scanner are determined through interaction of the ultrasound scanner with the fiducials 213. In one or more implementations, guiding the ultrasound scanner includes the step 502 of obtaining coordinates 504 of the ultrasound scanner with reference to the fiducials 213, a step 601 of calculating a distance from the coordinates of the ultrasound scanner to the coordinates of the modeled starting position, a step 602 of determining, based on the calculated distance, at least one of a frequency, volume, melody, or beat for an audio signal, and a step 603 of playing the audio signal through a speaker 600 operatively coupled in communication with the processor.

Other exemplary aspects of the invention provide a computer-implemented method 700 that includes a step 301 of obtaining a camera image 302 of a patient's body 212 within a space marked by fiducials 213. The method 500 also includes a step 304 of obtaining an ultrasound image 305 of a vascular structure within the patient's body. The method 500 also includes a step 402 of calculating, based on the camera image 302, a 3-D model 404 of the patient's body with reference to the fiducials 213, including coordinates 504 of an ultrasound scanner within the 3-D model. Further, the method 500 includes a step 704 of establishing a path 706 of the vascular structure within the 3-D model, based on the ultrasound image 305 and the coordinates 504 of the ultrasound scanner within the 3-D model. Then the method 500 includes a step 708 of determining coordinates 710 of a next optimal position for the ultrasound scanner, based on the path of the vascular structure and a vascular exam procedure to be performed; and a step 309 of guiding the ultrasound scanner to the coordinates 710 of the next optimal position.

In certain implementations, the step 309 of guiding the ultrasound scanner includes a step 418 of training a laser 207 on the coordinates 710 of the next optimal position, and a step 420 of illuminating a patient's body with the laser.

In certain implementations, guiding the ultrasound scanner includes obtaining coordinates 504 of the ultrasound scanner with reference to the fiducials 213.

In certain implementations, guiding the ultrasound scanner includes a step 506 of displaying an icon 210 for the ultrasound scanner coordinates 504 and an icon 211 for the modeled starting position 412 at a visual display 208 that is operatively coupled in communication with the processor 96. For example, in some implementations the coordinates 504 of the ultrasound scanner are determined through interaction of the ultrasound scanner with the fiducials 213.

In certain implementations, guiding the ultrasound scanner includes a step 601 of calculating a distance from the coordinates of the ultrasound scanner to the coordinates of the modeled starting position, as well as a step 602 of determining, based on the calculated distance, at least one of a frequency, volume, melody, or beat for an audio signal. In such implementations, guiding the ultrasound scanner also includes a step 603 of playing the audio signal through a speaker operatively coupled in communication with the processor.

Certain aspects of the invention provide an apparatus 200, which includes a memory 28 storing computer executable instructions 40; a camera 203; an ultrasound scanner 214; and at least one processor 16, coupled to the memory 28. The at least one processor 16 is configured according to the computer executable instructions 40 to facilitate a method 300. The method 300 includes a step 301 of obtaining from the camera 203 a camera image 302 of a patient's body 212 within a space marked by fiducials 213, as well as a step 402 of calculating, based on the camera image 302, a 3-D model 404 of the patient's body with reference to the fiducials 213. The method 300 further includes a step 406 of establishing, based on a vascular exam to be performed 205 and with reference to a 3-D template of human anatomy 204, a template starting position 408 for placing an ultrasound scanner on the 3-D template. The method 300 also includes a step 410 of mapping the template starting position from the 3-D template 204 to a modeled starting position 412 on the 3-D model 404 of the patient's body, and a step 414 of determining coordinates 416 of the modeled starting position 412 within the 3-D model 404 with reference to the fiducials 213. Additionally, the method 300 includes a step 303 of guiding the ultrasound scanner to the coordinates 416 of the modeled starting position 412.

According to certain embodiments of the exemplary apparatus 100, guiding the ultrasound scanner includes the processor facilitating a step 418 of operating motors to train a laser 207 to the coordinates 416 of the modeled starting position 412, and a step 420 of illuminating the patient's body with the laser.

According to one or more embodiments of the exemplary apparatus, guiding the ultrasound scanner includes the processor facilitating a step 502 of obtaining coordinates 504 of the ultrasound scanner with reference to the fiducials 213, and displaying an icon 210 for the ultrasound scanner coordinates and an icon 211 for the modeled starting position 412 at a visual display 208 that is operatively coupled in communication with the processor 16.

According to one or more embodiments of the exemplary apparatus 200, guiding the ultrasound scanner 214 includes the processor 16 facilitating the step 502 of obtaining coordinates 504 of the ultrasound scanner with reference to the fiducials 213, as well as a step 601 of calculating a distance from the coordinates of the ultrasound scanner to the coordinates of the modeled starting position. Additionally, according to one or more embodiments of the apparatus, the processor facilitates the step 602 of determining, based on the calculated distance, at least one of a frequency, volume, melody, or beat for an audio signal; and the step 603 of playing the audio signal through a speaker operatively coupled in communication with the processor.

Other embodiments of the invention provide an apparatus 200, which includes a memory 28 storing computer executable instructions 40; a camera 203; an ultrasound scanner 214; and at least one processor 16, coupled to the memory 28, and configured according to the computer executable instructions to facilitate a method 300. The method 300 includes a step 301 of obtaining from the camera 203 a camera image 302 of a patient's body 212 within a space marked by fiducials 214, and includes a step 304 of obtaining from the ultrasound scanner 214 an ultrasound image 305 of a vascular structure within the patient's body. The method 300 also includes a step 402 of calculating, based on the camera image 302, a 3-D model 404 of the patient's body with reference to the fiducials 213, including coordinates 504 of the ultrasound scanner within the 3-D model. The method 300 also includes a step 704 of establishing a path 706 of the vascular structure within the 3-D model 404, based on the ultrasound image 305 and the coordinates of the ultrasound scanner 504 within the 3-D model 404. Additionally, the method 300 includes a step 708 of determining coordinates 710 within the 3-D model of a next optimal position for the ultrasound scanner, based on the path 706 and the vascular exam procedure 205 to be performed. Finally, the method 300 includes a step 309 of guiding the ultrasound scanner 214 to the coordinates 710 of the next optimal position. According to one or more embodiments, guiding the ultrasound scanner includes the processor facilitating the step 418 of operating motors to direct a laser 207 to the coordinates of the modeled starting position; and facilitating the step 420 of illuminating the patient's body with the laser 207. According to one or more embodiments, guiding the ultrasound scanner includes the processor facilitating the step 502 of obtaining coordinates 504 of the ultrasound scanner 214 with reference to the fiducials 213. According to one or more embodiments, guiding the ultrasound scanner includes the processor facilitating the step 506 of displaying an icon 210 for the ultrasound scanner coordinates and an icon 211 for the modeled starting position at a visual display 208 that is operatively coupled in communication with the processor 16. According to one or more embodiments, guiding the ultrasound scanner includes the processor facilitating the step 601 of calculating a distance from the coordinates of the ultrasound scanner to the coordinates of the modeled starting position; the step 602 of determining, based on the calculated distance, at least one of a frequency, volume, melody, or beat for an audio signal; and the step 603 of playing the audio signal through a speaker operatively coupled in communication with the processor.

One or more embodiments of the invention, or elements thereof, can be implemented in the form of an apparatus including a memory and at least one processor that is coupled to the memory and operative to perform exemplary method steps. FIG. 10 depicts a computer system that may be useful in implementing one or more aspects and/or elements of the invention, also representative of a cloud computing node according to an embodiment of the present invention. Referring now to FIG. 10, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 10, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 10) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 1-2 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
determining an optimal position for placement of an ultrasound scanner on a patient's body, in response to at least a stereoscopic camera image, a database of human anatomy that includes a 3-D template of vasculature, an exam procedure, and patient information, wherein the camera image includes the exterior of the patient's body and a plurality of fiducials that mark a space containing the patient's body, wherein the fiducials are displaced from the patient's body and are stationary in the space containing the patient's body, wherein determining the optimal position includes:
   establishing in a computer memory, by operation of a processor, a 3-D model of the patient's body with reference to the fiducials based on the camera image, wherein the 3-D model of the patient's body is established by computer image analysis of the camera image with reference to the fiducials in the camera image,
   mapping a template starting position from the 3-D template to a modeled starting position on the 3-D model of the patient's body, and
   determining first coordinates, using the 3-D model of the patient's body, of the modeled starting position with reference to the fiducials;
determining second coordinates of the ultrasound scanner in the space containing the patient's body;
confirming, based on a comparison of the first coordinates and the second coordinates, that the ultrasound scanner is located at the optimal position on the patient's body;
obtaining an ultrasound image of a vascular structure within the patient's body with the ultrasound scanner positioned at the optimal position;
establishing in the computer memory an update of the 3-D model of the patient's body that establishes a path of the vascular structure based on the ultrasound image and the position of the ultrasound scanner; and
determining a next optimal position for placement of the ultrasound scanner on the patient's body, based on the path of the vascular structure.

2. The method of claim 1 further comprising training a visual indicator on the patient's body to the first coordinates of the modeled starting position, wherein training the visual indicator comprises illuminating the patient's body with a laser at the optimal position.

3. The method of claim 1 further comprising displaying at a display an image of the patient's body and on the image of the patient's body a first icon marking the coordinates of the ultrasound scanner with reference to the fiducials and a second icon marking the optimal position for the ultrasound scanner.

4. The method of claim 1 further comprising:
assessing ultrasound data from the scanner for a vascular abnormality.

5. The method of claim 4 further comprising:
determining an estimate of a degree of stenosis or occlusion; and
incorporating the estimate into the patient information.

6. The method of claim 4 further comprising:
outputting an alert indicating a presence of the vascular abnormality.

7. The method of claim 6 wherein outputting the alert comprises illuminating the patient's body with a laser at an approximate location of the vascular abnormality using a blink pattern or color distinct from any pattern or color used for guiding the ultrasound scanner.

8. A computer-implemented method comprising:
obtaining, at a processor operatively coupled in communication with a camera, a stereoscopic camera image of the exterior of a patient's body and of a plurality of fiducials that are displaced from the patient's body and mark a space containing the patient's body;
calculating, in the processor, based on computer image analysis of the camera image, a 3-D model of the patient's body with reference to the fiducials;
establishing, in the processor, based on a 3-D template of human anatomy and the 3-D model of the patient's body, a path of a modeled vascular structure;
establishing, in the processor, based on a vascular exam to be performed and with reference to the path of the modeled vascular structure, a modeled starting position on the 3-D model of the patient's body, wherein the modeled starting position is established as coordinates with reference to the fiducials by mapping a template starting position from the 3-D template to the modeled starting position on the 3-D model of the patient's body, and determining first coordinates, using the 3-D model of the patient's body, of the modeled starting position with reference to the fiducials;
confirming that the ultrasound scanner is at a position on the patient's body that corresponds to the first coordinates of the modeled starting position, wherein confirming that the ultrasound scanner is at the position on the patient's body includes determining second coordinates of the ultrasound scanner in the space containing the patient's body and comparing the first coordinates to the second coordinates;
obtaining an ultrasound image of the patient's body;
establishing an updated path of the modeled vascular structure, by operation of a neural network in the processor on the ultrasound image of the patient's body;
updating the 3-D model of the patient's body, based on the updated path of the modeled vascular structure; and
determining a next optimal position on the patient's body for the ultrasound scanner, based on the updated 3-D model.

9. The method of claim 8 wherein guiding the ultrasound scanner includes the processor operating motors to direct a laser to the coordinates of the modeled starting position and illuminating the patient's body with the laser.

10. The method of claim 8 wherein guiding the ultrasound scanner includes the processor:
displaying an icon for the ultrasound scanner coordinates and an icon for the modeled starting position, superimposed on the 3-D model, at a visual display that is operatively coupled in communication with the processor.

11. The method of claim 8 wherein guiding the ultrasound scanner includes the processor:
calculating a distance from the coordinates of the ultrasound scanner to the coordinates of the modeled starting position;
determining, based on the calculated distance, at least one of a frequency, volume, melody, or beat for an audio signal; and
playing the audio signal through a speaker operatively coupled in communication with the processor.

12. A computer-implemented method comprising:
obtaining a stereoscopic camera image of the exterior of a patient's body and of a space containing the patient's body and a plurality of fiducials that are displaced from the patient's body and mark the space;

calculating, based on the camera image, a 3-D model of the patient's body with reference to the fiducials;

establishing a path of a modeled vascular structure within the 3-D model of the patient's body, based on a 3-D template of human anatomy;

obtaining, from an ultrasound scanner, an ultrasound image of an actual vascular structure within the patient's body;

determining an optimal position of the ultrasound scanner on the patient's body by:

establishing in a computer memory, by operation of a processor, a 3-D model of the patient's body with reference to the fiducials based on the camera image, wherein the 3-D model of the patient's body is established by computer image analysis of the camera image with reference to the fiducials in the camera image, mapping a template starting position from the 3-D template to the optimal position on the 3-D model of the patient's body, and determining first coordinates, using the 3-D model of the patient's body, of the optimal position with reference to the fiducials;

determining second coordinates of the ultrasound scanner in the space containing the patient's body;

confirming, based on a comparison of the first coordinates and the second coordinates, that the ultrasound scanner is located at the optimal position on the patient's body;

establishing an updated path of the modeled vascular structure within the 3-D model, based on the ultrasound image, the 3-D template of human anatomy, and the coordinates of the ultrasound scanner within the space containing the patient's body;

determining coordinates, within the 3-D model, of a next optimal position on the patient's body for the ultrasound scanner, based on the updated path of the modeled vascular structure and a vascular exam procedure to be performed; and guiding the ultrasound scanner from the optimal position to the coordinates of the next optimal position on the patient's body.

13. The method of claim 12 wherein guiding the ultrasound scanner includes the processor:

operating motors to direct a laser to the coordinates of the next optimal position relative to the fiducials; and illuminating the patient's body with the laser.

14. The method of claim 13 wherein guiding the ultrasound scanner includes the processor:

displaying at a visual display that is operatively coupled in communication with the processor the map of the patient's body, a first icon for the coordinates of the ultrasound scanner within the map of the patient's body and a second icon for the coordinates of the next optimal position.

15. The method of claim 12 wherein guiding the ultrasound scanner includes the processor:

calculating a distance from the coordinates of the ultrasound scanner to the coordinates of the next optimal position;

determining, based on the calculated distance, at least one of a frequency, volume, melody, or beat for an audio signal; and playing the audio signal through a speaker operatively coupled in communication with the processor.

16. An apparatus comprising:
a memory storing computer executable instructions;
a camera;
an ultrasound scanner; and
at least one processor, coupled to the memory, and configured according to the computer executable instructions to facilitate a method comprising:

obtaining from the camera a stereoscopic camera image of the exterior of a patient's body and of a space containing the patient's body and a plurality of fiducials that are displaced from the patient's body and mark the space;

calculating, based on computer image analysis of the camera image, a 3-D model of the patient's body with reference to the fiducials;

establishing a path of a modeled vascular structure, based on a 3-D template of human anatomy, within the 3-D model of the patient's body;

establishing, based on a vascular exam to be performed and on the 3-D model of the patient's body, and with reference to the path of the modeled vascular structure, a modeled starting position for placing an ultrasound scanner on the patient's body, wherein the modeled starting position is established by mapping a template starting position from the 3-D template to the modeled starting position on the 3-D model of the patient's body, and determining first coordinates, using the 3-D model of the patient's body, of the modeled starting position with reference to the fiducials;

determining second coordinates of the ultrasound scanner in the space containing the patient's body;

guiding the ultrasound scanner to a position on the patient's body corresponding to the coordinates of the template starting position, wherein guiding the ultrasound scanner includes comparing the second coordinates to the first coordinates;

obtaining from the ultrasound scanner an ultrasound image of an actual vascular structure in the patient's body;

establishing an updated path of the modeled vascular structure, based on the ultrasound image of the actual vascular structure;

updating the 3-D model of the patient's body according to the updated path of the modeled vascular structure;

determining coordinates of a next optimal position on the patient's body for the ultrasound scanner, based on the updated 3-D model of the patient's body and path of the modeled vascular structure; and guiding the ultrasound scanner to the next optimal position on the patient's body.

17. The apparatus of claim 16 wherein guiding the ultrasound scanner includes the processor facilitating:

operating motors to direct a laser to the coordinates of the modeled starting position; and illuminating the patient's body with the laser.

18. The apparatus of claim 16 wherein guiding the ultrasound scanner includes the processor facilitating:

displaying an icon for the ultrasound scanner coordinates and an icon for the coordinates of the modeled starting position at a visual display that is operatively coupled in communication with the processor.

19. The apparatus of claim 16 wherein guiding the ultrasound scanner includes the processor facilitating:

calculating a distance from the coordinates of the ultrasound scanner to the coordinates of the modeled starting position;

determining, based on the calculated distance, at least one of a frequency, volume, melody, or beat for an audio signal; and playing the audio signal through a speaker operatively coupled in communication with the processor.

20. An apparatus comprising:

a memory storing computer executable instructions;

a camera;

an ultrasound scanner; and at least one processor, coupled to the memory, and configured according to the computer executable instructions to facilitate a method comprising:

obtaining from the camera a stereoscopic camera image of the exterior of a patient's body and of a space containing the patient's body and a plurality of fiducials that are displaced from the patient's body and mark the space;

determining coordinates of the ultrasound scanner in the space containing the patient's body;

calculating, based on the camera image, a 3-D model of the patient's body with reference to the fiducials;

establishing a path of a modeled vascular structure within the 3-D model, based on a 3-D template of human anatomy;

obtaining from the ultrasound scanner an ultrasound image of an actual vascular structure within the patient's body;

updating the 3-D model of the patient's body, based on the ultrasound image and the coordinates of the ultrasound scanner within the space containing the patient's body;

determining coordinates, within the 3-D model of the patient's body, of a next optimal position for the ultrasound scanner, based on the updated path of the modeled vascular structure and a vascular exam procedure to be performed, by mapping a template optimal position from the 3-D template to the next optimal position on the 3-D model of the patient's body, and determining the coordinates, using the 3-D model of the patient's body, of the next optimal position with reference to the fiducials; and guiding the ultrasound scanner to a position on the patient's body that corresponds to the coordinates of the next optimal position.

21. The apparatus of claim 20 wherein guiding the ultrasound scanner includes the processor facilitating:

operating motors to direct a laser to the coordinates of the modeled starting position; and illuminating the patient's body with the laser.

22. The apparatus of claim 20, further comprising a virtual reality headset visual display, wherein guiding the ultrasound scanner includes the processor facilitating:

displaying an icon for the ultrasound scanner coordinates and an icon for the modeled starting position at the virtual reality headset visual display that is operatively coupled in communication with the processor.

23. The apparatus of claim 20 wherein guiding the ultrasound scanner includes the processor facilitating:

calculating a distance from the coordinates of the ultrasound scanner to the coordinates of the modeled starting position;

determining, based on the calculated distance, at least one of a frequency, volume, melody, or beat for an audio signal; and playing the audio signal through a speaker operatively coupled in communication with the processor.

24. The method of claim 12 wherein guiding the ultrasound scanner includes a processor controlling motors of a robotic arm to move the ultrasound scanner to the next optimal position, the method further comprising:

assessing ultrasound data from the ultrasound scanner for a vascular abnormality at a current position of the ultrasound scanner; and the processor controlling a marker of the robotic arm to mark the patient's body at the current position of the ultrasound scanner.

25. The method of claim 8, wherein the coordinates of the modeled starting position are a position corresponding to a particular vessel in the modeled vascular structure, and the method further comprises determining the next optimal position by following a path along the particular vessel in the updated path of the modeled vascular structure.

\* \* \* \* \*